United States Patent [19]

Stephens et al.

[11] 4,294,799
[45] Oct. 13, 1981

[54] TEMPERATURE REGULATING APPARATUS

[75] Inventors: Donald E. Stephens, Palo Alto; John T. Taylor, Santa Clara, both of Calif.

[73] Assignee: Beckman Instruments, Inc., Fullerton, Calif.

[21] Appl. No.: 143,212

[22] Filed: Apr. 24, 1980

[51] Int. Cl.³ .............. G01N 31/22; G01N 31/08; G01J 3/46
[52] U.S. Cl. ............................ 422/62; 422/70; 422/109; 422/202; 73/61.1 C; 165/30
[58] Field of Search ............ 422/62, 69, 105, 70, 422/109, 202, 206, 55, 199; 73/61.1 C; 165/30, 26, 59, 60, 61

[56] References Cited

U.S. PATENT DOCUMENTS

| Re. 29,880 | 1/1979 | Duff | 422/109 X |
|---|---|---|---|
| 2,671,643 | 3/1954 | Gordon | 165/30 X |
| 3,010,798 | 11/1961 | Whitehead et al. | 406/410 X |
| 3,067,014 | 12/1962 | Morgan | 422/62 |
| 3,230,048 | 1/1966 | Skeggs | 422/70 |
| 3,285,055 | 11/1966 | Reinecke | 165/30 X |
| 3,375,080 | 3/1968 | Fujii et al. | 422/70 |
| 3,377,545 | 4/1968 | Tveit | 165/26 X |
| 3,377,817 | 4/1968 | Petranek | 165/26 X |
| 3,403,852 | 10/1968 | Gorchev | 165/26 X |
| 3,463,615 | 8/1969 | Sochor | 422/70 |
| 3,473,022 | 10/1969 | Walz et al. | 422/68 |
| 3,532,472 | 10/1970 | Foster | 422/62 |
| 3,590,910 | 7/1971 | Lorenz | 165/30 X |
| 3,806,321 | 4/1974 | Durrum et al. | 422/70 |
| 3,811,842 | 5/1974 | Diebler et al. | 422/109 X |
| 3,855,129 | 12/1974 | Abrahams et al. | 422/70 X |
| 3,918,907 | 11/1975 | Stephens | 73/61.1 C |
| 3,941,487 | 3/1976 | Ehret et al. | 73/61.1 C |
| 4,165,219 | 8/1979 | Huber | 422/70 X |
| 4,234,543 | 11/1980 | Matovich | 422/199 X |

Primary Examiner—Kenneth M. Schor
Attorney, Agent, or Firm—R. J. Steinmeyer; F. L. Mehlhoff; T. R. Schulte

[57] ABSTRACT

A temperature regulating apparatus which increases optical sensitivity and resolution of a liquid in a reaction chamber by heating while providing rapid cooling to prevent vaporization of the liquid within the reaction chamber. The apparatus includes a heat exchanger containing the reaction chamber and an insulating chamber surrounding the heat exchanger. A coolant may be passed through the heat exchanger to prevent boiling should a change in liquid flow make such occurrence likely. The change in liquid flow is monitored by an analyzer monitor, and the temperature in the reaction chamber is changed accordingly.

13 Claims, 5 Drawing Figures

TEMPERATURE REGULATING APPARATUS

BACKGROUND OF THE INVENTION

1. Field of the Invention

The invention relates to the field of liquid chromatographic analysis. More particularly the invention relates to temperature control in liquid chromatographic apparatus. By way of further characterization but not by way of limitation thereto, the invention is an apparatus for quickly reducing the temperature of the liquid flowing through the reactor of a liquid chromatography apparatus if conditions occur in the system which are conductive to boiling of the liquid.

2. Description of the Related Art

Amino acid analysis is a specialized application of a liquid column chromatographic separation technique which utilizes an ion-exchange resin as the stationary phase, with eluting buffers of varying pH and salt concentrations employing as the moving phase. Amino acids contained in a sample introduced onto the top of the chromatographic column are separated from each other as they are eluted through the resin bed which comprises the column packing. The amino acids present in the eluted stream are detected by combining the column effluent with a reagent which is metered into the stream at a fixed flow rate. The reagent, upon combining with amino acids present in the stream, forms compounds which, when subjected to a development process, can be detected by specific changes in optical properties such as absorbance or fluorescence. In the classical method developed by Stein and Moore, the reagent used is Ninhydrin dissolved in a suitable solvent/buffer solution. The development process consists of heating the solution at a fixed temperature for a specified period of time. The resulting compound has a specific color, the optical density of which is proportional to the concentration of the compound present in the flowing stream. The physical property measured is then optical absorbance measured at a specific wavelength of light.

Calibration of an amino acid analyzer in terms of its specific sensitivity to detect amino acids is directly related to the color development process. That is, optimum color development requires maintaining the eluent/reagent mixture at an elevated temperature for a fixed period of time. In order for the instrument calibration to be stable, two parameters of the development process, temperature and exposure time, must remain stable. Prior devices have accomplished this by causing the effluent to pass through a capillary coil which has been suspended in a boiling water bath. The temperature of the liquid in the coil is determined by the boiling point of the water and development time is determined by the internal volume of the capillary and the volumetric flow rate of the liquid passing therethrough. Such a device is utilized in the apparatus disclosed in U.S. Pat. No. 3,010,798 issued to E. C. Whitehead et al. on Nov. 28, 1961. While a boiling water reactor provides a stable, low cost, thermostatting device, the exposure times required necessitate the use of long capillary coils. Thus, the clear resolution between amino acids as they are eluted from the column become diffused as they are pumped through these long capillaries. In addition, a long start-up time is necessary to bring the water to a boil.

Exposure of the eluent/reagent mixture to higher temperatures for a shorter period of time, as by using shorter capillary coils, will result in maximum sensitivity and improved resolution. However, as the temperature of the reaction coil is raised, care must be taken to prevent boiling of the liquid passing through the coil. Vapor bubbles formed in the line due to boiling may pass into the cuvette of the photometer which is used for the optical detection. The presence of vapor bubbles in a cuvette destroys the calibration of the instrument and causes large noise transients significantly affecting the accuracy of the instrument. One common cause for boiling is a drop in the flow rate of buffer or reagent in the system. This drop may be caused by pump failure, by exhaustion of the supply of the substance, etc. The change in composition of the eluent/reagent mixture changes the boiling point of the substance and may lower it sufficiently to allow boiling to occur. This problem necessitates the inclusion of a means for controlling the temperature of the reagent/eluent mixture to prevent vaporization of the mixture.

A device which incorporates such a system is shown in U.S. Pat. No. 3,806,321 issued to E. L. Durrum et al. on Apr. 23, 1974. That device provides a means for quenching the heat of the mixed materials in the coil in the event that they are overheated. In that device, when it is desired to cool the coil, a cooling liquid is forced from a reservoir below the coil into a reservoir above the coil. The cooling liquid is then allowed to drain over the coil and into the reservoir below the coil. A gas under pressure is connected to the lower reservoir and is used to force the liquid into the upper reservoir. While suited for its intended purpose, this device is limited in that it cannot be cycled very often because the cooling liquid does not cool fast enough to allow for repeated uses. In addition, the liquid must be contained in the reservoirs and requires elaborate containing equipment.

SUMMARY OF THE INVENTION

The invention is a temperature regulating device which allows concentrated heating of a liquid in a reaction chamber while providing a means for rapidly cooling the liquid when some system parameter changes to an extent that it could cause the liquid to boil and create vapor bubbles in the reaction vessel. The cooling device may be used as often and for as long as is needed since an outside source of coolant is used. There is no containment problem since ambient air or other gases which may be vented into ambient air are preferably used as the coolant.

The system includes means for regulating the temperature of the liquid contained within a reaction chamber and includes heat energy exchanging means surrounding the reaction chamber. The flow of the liquid through the system is monitored by a monitoring means. The reaction chamber and the heat energy exchanging means are substantially enclosed in a heat retaining means. The heat retaining means includes at least one movable portion above the reaction chamber. A means for introducing a coolant into the substantially enclosed space, defined by the heat retaining means, is responsive to the flow monitoring means and cooperative with the movable portion to allow for rapid cooling of the reaction chamber and the liquid contained therein should fluctuations in flow rate through the system present a danger of boiling.

In the preferred embodiment the reaction vessel is a capillary coil mounted in a heat exchanger. The heat exchanger is positioned in an insulating chamber having an open bottom portion. A damper on a top portion of the chamber opposite to the bottom portion and a fan near the bottom portion cooperate to remove heat from the heat exchanger thereby cooling the capillary coil and the substance contained therein. The heat exchanger includes a mandrel about which the capillary coil is wrapped. A heater is positioned in the mandrel adjacent the capillary coil. A temperature sensor is also positioned adjacent the capillary coil. A heat sink surrounds the mandrel and the capillary coil. The heat sink includes a container substantially enclosing the mandrel and the capillary coil such that the capillary coil is positioned therebetween. A heat transfer substance surrounds the capillary coil between the mandrel and the container. A plurality of heat radiating fins are connected to the container and extend into the substantially enclosed space defined by the insulating chamber.

The heater raises the temperature of the capillary coil and the substance contained therein to the desired level. A reaction controller receives feedback from an analyzer monitor and from the temperature sensor. The analyzer monitor indicates pump flow such that a decrease in buffer or reagent flow will cause the damper on the top portion of the chamber to cooperate with the fan to convey ambient air through the heat radiating fins. Heat may thus be rapidly removed from the heat exchanger and thus from the capillary coil and the substance contained therein. A reduction in reagent flow causing a lowering of the boiling point of the substance in the capillary coil will thus not result in boiling of the substance. The introduction of bubbles into the capillary coil and cuvette is thus prevented.

DESCRIPTION OF THE PREFERRED EMBODIMENT

Figure 1:
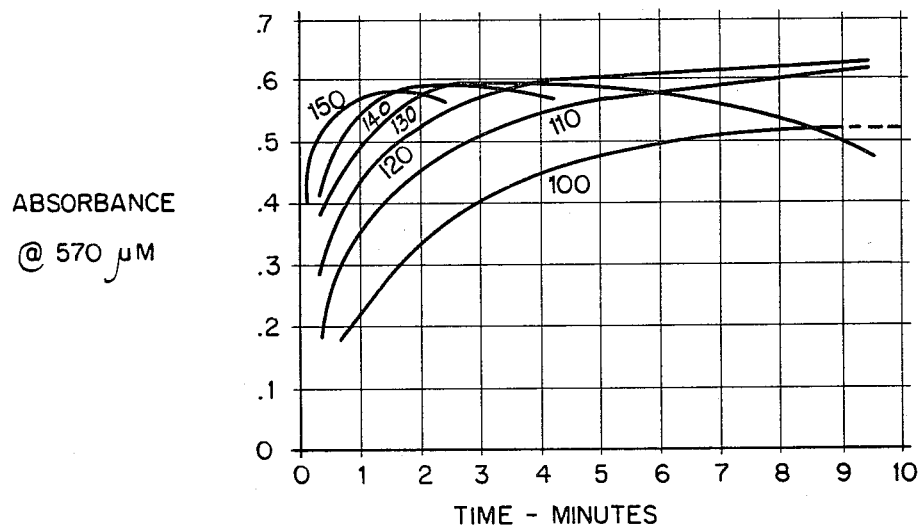
FIG. 1 is a graph of comparative eluent/reagent color development for variations in temperature and time.

Like reference numerals denote like structure throughout each of the various figures.

Figure 2:
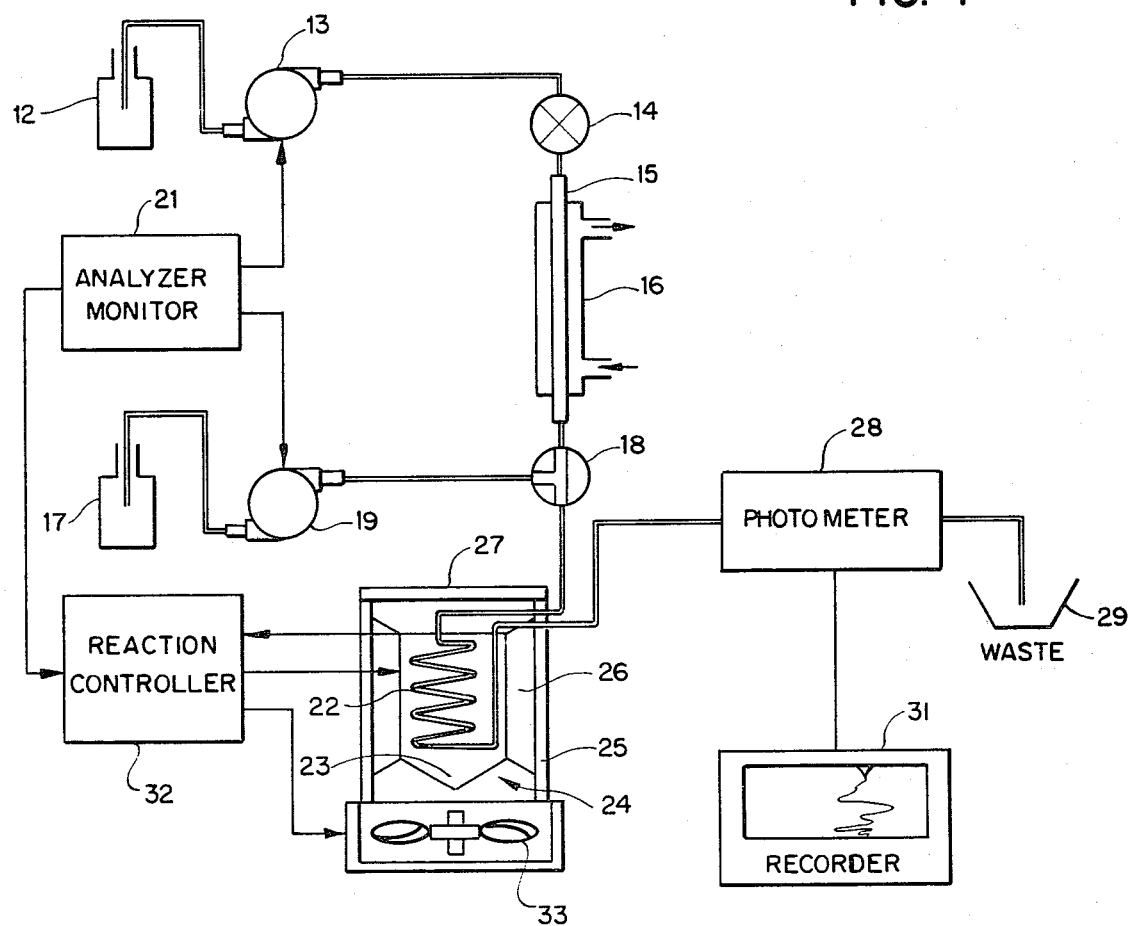
FIG. 2 is a schematic of an amino acid analyzer.

Referring to FIG. 2, a schematic of an amino acid analyzer is shown. A buffer solution 12 is conveyed by a pump 13 to a sample injector 14 where it is mixed with a sample to be analyzed. The sample plus buffer solution is conducted to a chromatographic column 15. Column 15 is encased in a water jacket 16 for controlling the temperature of the column. The buffer and sample eluent emerges from column 15 and is combined with a reagent 17 at a mixing tee 18. Reagent 17 is moved to mixing tee 18 by a pump 19. The operating characteristics or pumping capacities of pump 19 and pump 13 are sensed by an analyzer monitor 21. The reagent/eluent solution is conveyed to a capillary coil 22. Capillary coil 22 is contained in a heat enclosure 23 which is itself contained in a substantially enclosed space 24 defined by an insulating chamber 25. A plurality of fins 26 extend and define a portion of the heat enclosure 23 within substantially enclosed space 24. A movable portion which may include a solenoid operated damper 27 is positioned on insulating chamber 25 above capillary coil 22. The reagent/eluent mixture, after traveling through capillary coil 22, moves to a photometer 28 and thence to waste collector 29. A recorder 31 may be connected to photometer 28 for providing a record of the photometer output. A reaction controller 32 is operatively associated with heat enclosure 23 and analyzer monitor 21. Reaction controller 32 also controls the introduction of coolant to the enclosure 23 as, for example, air flow by means of a fan 33.

Figure 3:
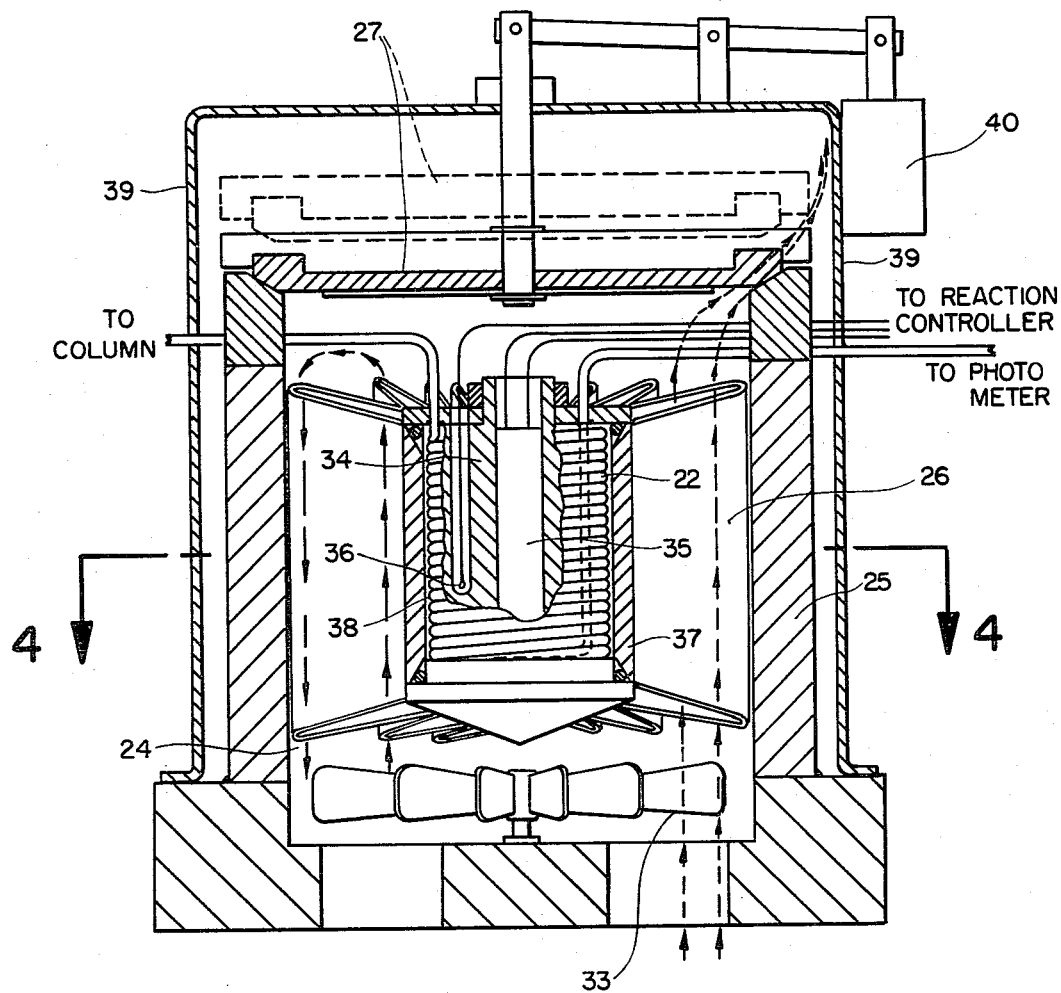
FIG. 3 is a side sectional view of the preferred embodiment of the invention.

Referring to FIG. 3, a side sectional view of insulating chamber 25 and a partial side sectional view of the heat exchanger are shown. Capillary coil 22 is wound on a mandrel 34. A heating means which may include a cartridge heater 35 is contained within mandrel 34. A temperature sensing means which may include a thermistor 36 is contained within mandrel 34 adjacent capillary coil 22. A heat energy exchanging means include mandrel 34, a container 37, a heat transferring substance 38, and heat radiating fins 26. Insulating chamber 25 defines a substantially enclosed space 24. Movable damper 27 may be opened by a solenoid 40. Solenoid 40 is supported on a narrow mounting strip 39.

Figure 4:
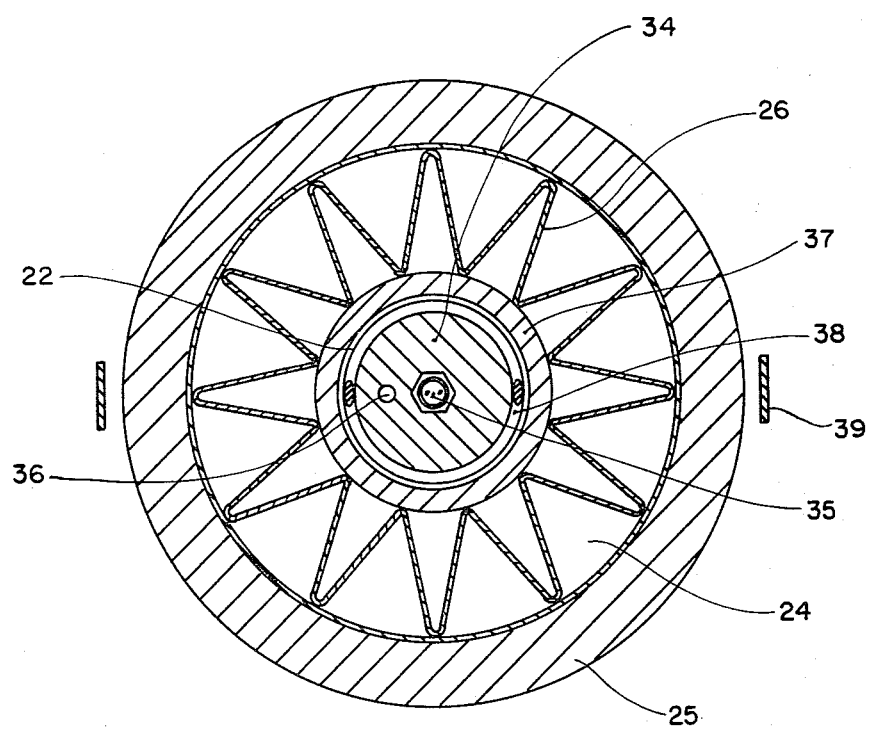
FIG. 4 is a top view of the invention through the sectional line 4—4 of FIG. 3.

Referring to FIG. 4, a view through section 4—4 of FIG. 3 is shown. Capillary coil 22 is wound on mandrel 34. Cartridge heater 35 and thermistor 36 are contained within mandrel 34. Fins 26 are attached to container 37. Substantially enclosed space 24 is defined by insulating chamber 25. Heat transferring substance 38 is contained between mandral 34 and container 37.

Figure 5:
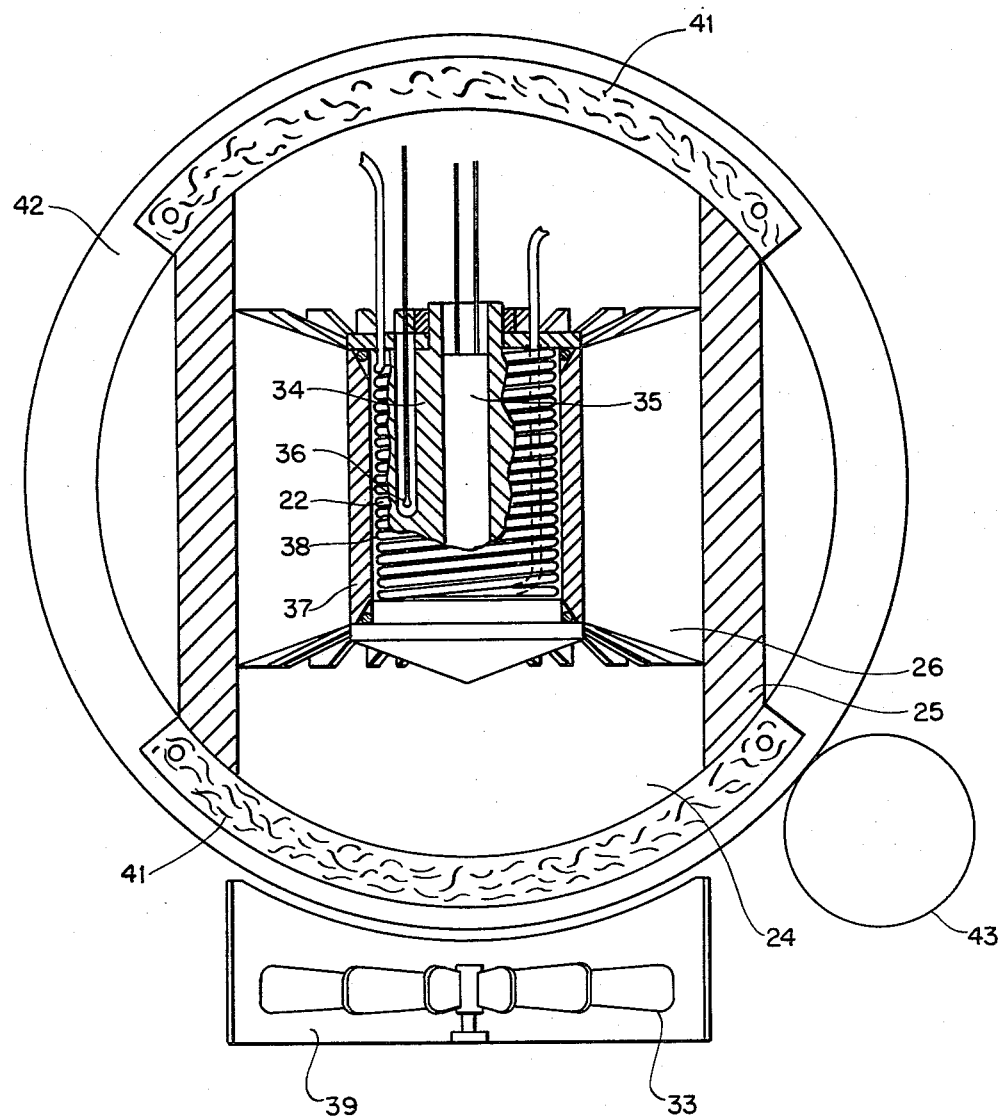
FIG. 5 is a side sectional view of an alternate embodiment of the invention.

Referring to FIG. 5, an alternate embodiment of the invention is shown. Capillary coil 22 is wound on mandrel 34. Cartridge heater 35 and thermistor 36 are contained within mandrel 34. Heat transferring substance 38 fills the interstices between mandrel 34 and container 37 not occupied by capillary coil 22. Insulating chamber 25 defines substantially enclosed space 24. Heat radiating fins 26 are connected to container 37. A movable portion includes a pair of insulating shutters 41 which are mounted on a circular support 42. Fan 33 is mounted on platform 39. Shutters 41 are driven by a drive wheel 43 which is itself driven by a unidirectional motor (not shown).

MODE OF OPERATION

Empirical studies have been made of color development for ninhydrin/amino acid compounds under various time and temperature conditions. The results of one such study are shown graphically in FIG. 1. FIG. 1 is a plot of optical density vs. exposure time for a family of curves produced at different temperatures. Referring to FIG. 1, it can be seen that to obtain maximum color development at 100° C. requires a dwell time of 15 minutes within the reactor. Equivalent development may be reached by heating the mixture to a higher temperature for a shorter period of time. For example, at 120° C. only two minutes are required for equivalent development.

Referring to FIG. 2, a schematic of the amino acid analyzer is shown. Buffer solution 12 is combined with the sample to be analyzed and this buffer/sample solution is conveyed into chromatographic column 15. The temperature of column 15 is maintained by circulating thermostated water through water jacket 16. The eluent from chromatographic column 15 is mixed with a reagent which may include a ninhydrin solution supplied by pump 19 to mixing tee 18. The ninhydrin/eluent mixture is conveyed to capillary coil 22. It is within capillary coil 22 that color development takes place. That is, after leaving capillary coil 22, the mixture is conveyed to photometer 28 where its optical properties are measured. The results are indicated on recorder 31. As discussed above, a shorter capillary coil and higher development temperature result in improved optical qualities for the ninhydrin/eluent mixture. The improved optical qualities result in greater accuracy and improved results for the amino acid analyzer. The shorter capillary coil and concentrated heating also result in quicker warm-up time as opposed to hot water bath systems.

Temperature control within insulating chamber 25 allows the use of higher temperature in capillary coil 22 which are necessary for better color development. Because temperature higher than those achieved with the conventional hot water bath are utilized, possible overheating, which introduces bubbles into the capillary coil, can be a problem. Generally, the boiling point of the buffer/sample solution is lower than that of the reagent/eluent solution. Thus, while the capillary coil and ninhydrin/eluent mixture contained therein must be heated for color development purposes, it is also important that a means for cooling the mixture be included in the device. Otherwise, a decrease in the flow of reagent could result in boiling of the solution. While boiling does not occur immediately, reduction of reagent flow may eventually result in boiling of the mixture. The cooling means prevents boiling and thus prevents bubbles from forming within the capillary coil. Once bubbles form they may be passed onto the cuvette where they interfere with the readings from the photometer. Once in a system these bubbles are difficult to remove, often requiring bleeding of the lines.

Referring to FIG. 3, the ninhydrin/eluent mixture is contained in capillary coil 22. Cartridge heater 35 is contained in mandrel 34 such that mandrel 34 conducts heat energy to capillary coil 22. Thermistor 36 indicates the temperature of mandrel 34 adjacent capillary coil 22 and provides feedback to reaction controller 32 to regulate power to heater 35. A decrease in, or loss of, reagent flow detected by monitor 21 causes controller 32 to reduce the temperature set point of reactor 25 through heater 35 and thermistor 36.

The flow of heat to and from the capillary coil 22 is facilitated by the heat exchanging means. A heat transferring substance such as, for example, silicone oil or a eutectic alloy 38 is inserted into the spaces between mandrel 34 and container 37 not occupied by capillary coil 22. The eutectic alloy assures good thermal contact between mandrel 34, capillary coil 22, and container 37. The cavity between mandrel 34 and container 37 is provided with a liquid tight seal by O-rings at the top and bottom. The cavity is then evacuated and filled with the heat transferring substance. Heat radiating fins 26 are preferably aluminum for optimum heat conduction and are connected to container 37. Thus, heat from heating means 35 may be conveyed through mandrel 34 to capillary coil 22 and through eutectic alloy 38 to container 37 and thence to heat radiating fins 26. Fins 26 are open at the top and bottom to allow air flow through as well as around them.

Cartridge heater 35 is used to raise the temperature of capillary coil 22 and the ninhydrin/eluent substance contained therein. The color development process for the ninhydrin/eluent substance is thus enhanced. If ninhydrin flow is reduced or is stopped entirely, either intentionally or due to system failure, then the liquid mixture may boil, thus introducing bubbles into the system. This is because reduced flow changes the constitution of the eluent/reagent mixture and thus changes the boiling point of the mixture as it passes through capillary coil 22. The lowered boiling point may result in vapor bubble formation. If the analyzer monitor 21 detects that the flow rate of liquid through pump 19 or pump 13 is stopped or reduced to any great extent then the fan 33 is activated by reaction controller 32 in response to a signal from analyzer monitor 21 indicating such flow rate change. Capillary coil 22 is thus rapidly cooled by the air flow from fan 33 with damper 27 opened thereby preventing boiling of the substance contained therein. Because ambient air is used as the heat exchange substance, there is no need to contain a heat exchange liquid as with prior devices.

To cool the reactor, fan 33 draws ambient air into substantially enclosed space 24 and damper 27 is opened (as indicated by dotted line in FIG. 3) to allow the passage of the ambient air through substantially enclosed space 24 and heat radiating fins 26 as illustrated by the broken line arrows in FIG. 3. This heated air is vented around strip 39. Damper 27 is moved by solenoid 40 in the preferred embodiment although it could be moved by any conventional means. Because of the excellent thermal contact throughout the heat exchanging means, the ambient air introduced by fan 33 rapidly carries away heat from the heat exchanging means. The temperature of capillary coil 22 and the solution contained therein may thus be rapidly reduced, thus preventing the solution from reaching the critical point where boiling may occur and alleviating the problem of bubbles being introduced into the system.

It is recognized that, even with damper 27 closed, some heat convection occurs. That is, because insulating chamber 25 has an open bottom adjacent fan 33, some ambient air may be introduced into the system even when fan 33 is off. The solid line arrows on the left in FIG. 3 indicate the path of this ambient air. The air adjacent container 37 is heated and rises toward damper 27. The air is then cooled as it passes by the walls of insulating chamber 25 and the air settles back to the bottom of substantially enclosed space 24. There is thus some heat loss from the system but this is negligible when compared with the total amount of heat energy contained within the system.

In the preferred embodiment reaction controller 32 has two set points, one fixed at 95° C., and one adjustable from 95° C. to 135° C. Tests have shown that the heater 35 will heat the solution from 20° C. to 135° C. in 15 minutes and the air flow produced by fan 33 will cool the reaction coil from 135° C. to 95° C. in less than one minute. The system will recover from 95° C. to 135° C. in three minutes and will cool from 135° C. to 95° C. with only convection cooling in two minutes i.e. with the damper 27 open and the heater 35 turned off. If either pump is turned off or the reactor flow shows a drop in flow rate then the reaction controller 32 automatically initiates cooling of the reactor to 95° C. This rapid heating and cooling allows precise control of the temperature of the solution within the capillary coil. Thus, the development of the optical properties within the solution is enhanced by heating while the ability to cool rapidly prevents vaporization of the solution and precludes bubbles from forming within the capillary coil.

A pressure head is required to move fluid through the reactor and downstream photometer. The pressure required is dependent upon the viscosity of the fluid being pumped and may range from 100 psig for the buffer-reagent mixture to approximately 20 psig for buffer only. This elevated pressure serves to increase the boiling point of the fluids being pumped through the reactor. During routine operation, the buffer/reagent solution may be flushed out using clear buffer. This will be accompanied by a reduction in head pressure and attendant lowering of the boiling temperature as the reagent is moved through the reactor. With the present invention the rapid cooling ability of the system prevents boiling of the liquid as this pressure is reduced.

An alternate embodiment of the invention is shown in FIG. 5. The construction of the device within substantially enclosed space 24 is similar to that of FIG. 3. The essential difference between the embodiment shown in FIG. 5 and that of FIG. 3 lies in the construction of movable portion 27. In FIG. 5 the movable portion includes insulating shutters 41 attached to circular supports 42 at both the top and bottom of insulating chamber 25. In the closed position as shown in FIG. 5, substantially enclosed space 24 is sealed from ambient air at both the top and bottom. Shutters 41 are made of compliant material which forms a drafttight seal with insulating chamber 25. Circular supports 42, mounted on bearings (not shown), rotate shutters 41 such that shutters 41 may be moved to the sides of chamber 25. Shutters 41 are driven by drive wheel 43. The open and closed positions for shutters 41 are fixed by a microswitch which is operated by notches in circular supports 42. When shutters 41 are rotated the top and bottom of insulating chamber 25 are open, allowing fan 33 to force ambient air through substantially enclosed space 24. The ambient air is introduced through the bottom of insulating chamber 25 and exits through the top of insulating chamber 25. The embodiment shown in FIG. 5 seals both the top and bottom of insulating chamber 25 and thus eliminates the small convection heat loss encountered with the embodiment shown in FIG. 3. Additionally, fins 26 in FIG. 5 are solid extensions as opposed to the hollow fins employed in FIG. 3. The embodiment shown in FIG. 3 is preferred to that shown in FIG. 5 because the embodiment shown in FIG. 5 is more expensive and more complicated to operate.

While particular forms of the invention have been disclosed with respect to a preferred embodiment thereof, it is not to be so limited as changes and modifications may be made without departing from the scope of the invention. For example, carbon dioxide gas may be used instead of ambient air as the cooling substance. This would require a source of carbon dioxide to be vented into substantially enclosed space 24. While ninhydrin has been disclosed as the reagent to be mixed with the eluent from the chromatographic column, it should be understood that any suitable reagent may be used. Additionally, while the device has been disclosed as used in an amino acid analyzer, it should be expressly understood that the device may be used in any apparatus where temperature control of a substance within a reaction vessel is desired. A capillary coil has been disclosed as the reaction vessel with the present system. However, the concept could also be utilized if a different type of reaction vessel were employed.

The foregoing description, taken together with the appended claims, constitutes a disclosure which enables one skilled in the art and having the benefits of the teachings contained therein to make and use the invention. Further, the structure herein described constitutes a meritorious advance in the art which is unobvious to such skilled workers not having the benefit of these teachings.

What is claimed is:
1. An apparatus for preventing boiling of a liquid flowing through a heated reaction chamber of a liquid chromatograph instrument due to a change in the boiling point of said liquid, said apparatus comprising:
   said heated reaction chamber;
   means, adjacent said reaction chamber, for exchanging heat to and from said reaction chamber;
   means, associated with said flowing liquid, for monitoring a change in the ratio of reactants in said flowing liquid, said change in the ratio of reactants resulting in a change in the boiling point of said flowing liquid;
   means, defining a substantially enclosed space containing said reaction chamber and said heat exchanging means, for retaining heat;
   means, responsive to said monitoring means, for introducing a coolant into said substantially enclosed space in response to a change in said boiling point; and
   means defining an exit for said coolant from said enclosed space.
2. Apparatus according to claim 1 wherein said heat retaining means includes an insulating chamber having a substantially open bottom portion.
3. Apparatus according to claim 2 wherein said heat retaining means includes a solenoid operated damper mounted on a top portion of said chamber opposite to said substantially open bottom portion and moveable into open and closed positions with respect to said exit.
4. Apparatus according to claim 1 wherein said coolant includes ambient air.
5. Apparatus according to claim 1 wherein said coolant includes carbon dioxide gas.
6. Device according to claim 2 wherein the aforesaid coolant introducing means includes:
   a fan positioned adjacent said substantially open bottom portion; and
   a reaction controller effectively connected to said fan.
7. Device according to claim 1 wherein said reaction chamber includes a capillary coil.
8. Device according to claim 7 wherein the aforesaid heat exchanging means includes:
   a mandrel around which said capillary coil is wrapped;
   a container substantially enclosing said mandrel so as to define a substantially enclosed volume surrounding said mandrel, said capillary coil and a heat transferring substance being located in said substantially enclosed volume; and
   a plurality of heat radiating fins connected to said container.
9. Device according to claim 1 wherein said heat retaining means includes:
   an insulating chamber having an open top portion and an open bottom portion; and
   said at least one movable portion including a pair of rotatable shutters, one of said shutters substantially sealing said open top portion and the other of said shutters substantially sealing said open bottom portion.

10. An apparatus for preventing boiling of a liquid flowing through a heated reaction chamber in a liquid chromatograph instrument due to a change in the boiling point of said liquid flowing therethrough, said apparatus comprising:

said heated reaction chamber;

a flow monitor associated with said flowing liquid for monitoring a change in the ratio of reactants in said flowing liquid, said change in the ratio of reactants resulting in a change in the boiling point of said flowing liquid;

an insulating chamber containing said reaction chamber;

a damper on a top portion of said insulating chamber above said reaction chamber;

means, responsive to said flow monitor, for introducing a coolant into said insulating chamber and cooling said reaction chamber in response to a change in said boiling point;

means defining a heat enclosure positioned in said insulating chamber and containing said reaction chamber; and means defining an exit for said coolant from said insulating chamber.

11. Apparatus according to claim 10 wherein said heat enclosure includes:

a mandrel adjacent said reaction chamber; and a heat sink surrounding said mandrel and said reaction chamber.

12. Apparatus according to claim 11 wherein said heat sink includes:

a container substantially enclosing said mandrel so as to define a substantially enclosed volume surrounding said mandrel, said reaction chamber and a heat transferring substance being located in said substantially enclosed volume; and a plurality of heat radiating fins connected to said container.

13. Apparatus according to claim 10 wherein said cooling means includes:

a fan; and a reaction controller connected to said fan.

* * * * *